(12) United States Patent
Berlinger et al.

(10) Patent No.: US 8,693,763 B2
(45) Date of Patent: Apr. 8, 2014

(54) METHOD AND DEVICE FOR DETERMINING PREFERRED ALIGNMENTS OF A TREATMENT BEAM GENERATOR

(75) Inventors: Kajetan Berlinger, München (DE); Stephan Froehlich, Aschheim (DE)

(73) Assignee: Brainlab AG, Feldkirchen (DE)

( * ) Notice: Subject to any disclaimer, the term of this patent is extended or adjusted under 35 U.S.C. 154(b) by 315 days.

(21) Appl. No.: 12/769,971

(22) Filed: Apr. 29, 2010

(65) Prior Publication Data
US 2010/0278414 A1    Nov. 4, 2010

Related U.S. Application Data

(60) Provisional application No. 61/173,674, filed on Apr. 29, 2009.

(30) Foreign Application Priority Data

Apr. 29, 2009  (EP) ..................................... 09159002

(51) Int. Cl.
   *G06K 9/00*     (2006.01)
(52) U.S. Cl.
   USPC ........................................................ 382/152
(58) Field of Classification Search
   USPC ................................... 382/151, 152, 132, 128
   See application file for complete search history.

(56) References Cited

U.S. PATENT DOCUMENTS

| 5,513,238 A | 4/1996 | Leber et al. |
| 6,307,914 B1 * | 10/2001 | Kunieda et al. ................. 378/65 |
| 2008/0192893 A1 * | 8/2008 | Gertner .......................... 378/65 |
| 2008/0287728 A1 * | 11/2008 | Mostafavi et al. ................ 600/2 |
| 2008/0310590 A1 | 12/2008 | Meyer et al. |
| 2009/0060311 A1 * | 3/2009 | Mostafavi ..................... 382/132 |

FOREIGN PATENT DOCUMENTS

| EP | 7 832 313 | 9/2007 |
| EP | 2 070 478 | 6/2009 |

OTHER PUBLICATIONS

Robottom et al., "Improvements in prostate radiotherapy from the customization of beam directions", Medical Physics, vol. 25, No. 7, Jul. 1998, pp. 1171-1179.

* cited by examiner

*Primary Examiner* — Tarifur Chowdhury
*Assistant Examiner* — Abdullahi Nur
(74) *Attorney, Agent, or Firm* — Tucker Ellis LLP

(57) ABSTRACT

The present invention relates to a method for determining preferred alignments of a treatment beam generator, which is suitable for irradiating an object, relative to a body, wherein the visibility of the object in at least one image is taken into account when determining the preferred alignments, wherein the image is obtained by means of at least one imaging device, the position of which relative to the treatment beam generator is known and invariable.

15 Claims, 2 Drawing Sheets

METHOD AND DEVICE FOR DETERMINING PREFERRED ALIGNMENTS OF A TREATMENT BEAM GENERATOR

RELATED APPLICATION DATA

This application claims the priority of U.S. Provisional Application No. 61/173,674, filed on Apr. 29, 2009, which is hereby incorporated in its entirety by reference.

FIELD OF THE INVENTION

The present invention relates to a method and device for determining preferred alignments of a treatment beam generator, which is suitable for irradiating an object, relative to a body.

BACKGROUND OF THE INVENTION

Irradiating an object which is situated in or on a body, for example a tumor, with a treatment beam is known in medical applications. The treatment beam usually exhibits energies in the mega-electron volt (MeV) range, wherein planing the irradiation such that organs at risk (OAR) are not exposed to the treatment beam or are exposed as little as possible is known.

Recently, development has moved towards verifying the location of the object relative to the plan in real time during irradiation and guiding the treatment beam and/or switching it on or off when the object is situated in and/or departs from the beam path of the treatment beam. X-ray devices, the position of which relative to the treatment beam generator is known and invariable, are usually used for determining the location of the object during irradiation. The treatment beam generator and the x-ray device are for example arranged on the same support, which can be positioned relative to the body.

SUMMARY OF THE INVENTION

It is the object of the present invention to provide a method and device by which ascertaining the location of the object is improved.

This object is solved in accordance with the invention by: a method for determining preferred alignments of a treatment beam generator, which is suitable for irradiating an object, relative to a body, wherein the visibility of the object in at least one image is taken into account when determining the preferred alignments, wherein the image is obtained by means of at least one imaging device, the position of which relative to the treatment beam generator is known and invariable; by a computer program which, when it is executed in a computational unit, causes the computational unit to perform the above method; and by a device for determining preferred alignments of a treatment beam generator, which is suitable for irradiating an object, relative to a body, comprising a computational unit which is designed to take into account the visibility of the object in at least one image when determining the preferred alignments, wherein the image is obtained by means of at least one imaging device, the position of which relative to the treatment beam generator is known and invariable. The invention also relates to a treatment device. Advantageous embodiments may be gathered from the dependent claims.

The method in accordance with the invention relates to determining preferred alignments of a treatment beam generator, which is suitable for irradiating an object, relative to a body. In accordance with the invention, the visibility of the object in at least one image is taken into account when determining the preferred alignments. The image is obtained by means of at least one imaging device, the position of which relative to the treatment beam generator is known and invariable.

When conventionally planning an irradiation, only organs at risk are taken into account, and alignments of the treatment beam generator are selected at which the radiation exposure of organs at risk is minimized. Since the treatment beam generator and the imaging devices, for example in the form of x-ray devices, exhibit an invariable position relative to each other, the situation can arise whereby at the selected alignment of the treatment beam generator, the object is hidden in the images of the imaging devices by blocking structures (BS). Blocking structures, such as for example bones, exhibit a high density, such that the object cannot be resolved by the x-ray device. Using the method in accordance with the invention, the visibility of the object in the images of the imaging devices is taken into account when planning the irradiation, i.e. when determining the preferred alignment of the treatment beam generator. This means that the alignments which are determined as preferred alignments are those at which the object is easily visible in the images and the location of the object can thus be reliably ascertained.

The term "alignment" includes in particular the angle of incidence of the treatment beam onto the body in one or two degrees of freedom, but can optionally also include the translational alignment in one, two or three degrees of freedom. One rotational degree of freedom is for example the rotational angle of the treatment beam generator about a rotational axis which is for example the longitudinal axis of the body or an axis parallel to this, wherein the treatment beam preferably intersects said rotational axis. The second degree of freedom is for example a tilting angle about an axis which is perpendicular to the treatment beam and preferably intersects the longitudinal axis at a right angle. A movement about the tilting axis can be generated either by a movement of the beam generator or by moving a bearing surface on which the body is lying.

Preferably, organs at risk in the beam path of the treatment beam generator are taken into account when determining the preferred alignments. Thus, in addition to the visibility of the object, the organs at risk are also incorporated into planning the irradiation. The alignments which are determined as preferred alignments are particularly preferably those at which the treatment beam of the treatment beam generator hits as few organs at risk as possible and at which the greatest possible visibility of the object in the images of the imaging devices is simultaneously obtained, wherein the determination is for example made in two stages. In a first step, a number of alignments are determined at which the treatment beam hits as few organs at risk as possible. In a second step, one or more alignments in which the visibility of the object in the images is at a maximum are determined from said number of alignments. This gives highest priority to avoiding the irradiation of organs at risk.

Alternatively, an alignment of the treatment beam generator is assigned a value which is compiled from the organs hit by the treatment beam and the visibility of the object in the images, wherein the organs are for example grouped into risk groups, wherein an organ which is significantly at risk from the treatment beam results in a low value and vice versa. Weighting the risk to the organs and the visibility of the object when determining the value is left to the implementing person skilled in the art, for example in accordance with the type of object and/or treatment beam generator. The alignment having the highest value is in particular determined as a preferred alignment.

In one embodiment of the method, an image data set is provided which represents a three-dimensional image of at least a part of the body containing the object. The image is for example recorded by means of computed tomography (CT) or magnetic resonance tomography (MRT). The visibility of the object is determined from a virtual image which is calculated from the image data set. Calculating a virtual image, for example a projection in the form of a DRR (digitally reconstructed radiograph) from a three-dimensional image data set is known from the prior art. The virtual viewing angle from which the virtual image is calculated corresponds to the viewing direction of the imaging device for the corresponding alignment of the treatment beam generator. Since the relative position between the imaging device or devices and the treatment beam generator is known, the viewing direction of the imaging device(s) automatically follows from the alignment of the treatment beam generator.

Correspondingly, it is not the actual images of the imaging devices which are taken into account when determining the preferred alignments but rather the virtual images which are calculated from the image data set obtained prior to irradiation. This allows the irradiation angle to be planned before the patient is brought into contact with the treatment device.

Where data, regions, ranges or images are "provided", this means that they are ready for use by the method in accordance with the invention. The data or images can achieve this state of being "provided" by for example being detected or captured (for example by analysis apparatuses) or by being input (for example via interfaces). The data can also have this state by being stored in a memory (for example a ROM, CD and/or hard drive) and thus ready for use within the framework of the method in accordance with the invention. The data or images can also be determined, in particular calculated, in a step of the method before being provided, in particular before being stored.

In a continuation of the invention, the position of the object is determined from the image data set and/or the images of the imaging devices. The body, a part of a device—for example, the treatment beam generator—or any spatially fixed coordinate system serves for example as a reference point for the position of the object. The term "position" includes at least the location and preferably also the spatial alignment of the object.

The position of the object is for example determined by means of image fusion, wherein the image data set is distorted and/or virtually positioned such that virtual images calculated from the image data set modified in this way match the images of the imaging devices as well as possible. The position of the object then follows from the position of the object in the modified image data set. Other methods for ascertaining the position of an object on the basis of images from imaging devices are for example known from European patent applications EP 08 169 422.6 and EP 07 150 014.4 belonging to the Applicant.

Preferably, the treatment beam of the treatment beam generator is automatically switched and/or guided in accordance with the position of the object. This is particularly advantageous if the object moves during irradiation, for example due to a patient's breathing. If the treatment beam is switched, this means that the treatment beam is switched on when the object is situated in the beam path and switched off when the object is not lying in the beam path of the treatment beam. This is also referred to as "gating". If the treatment beam is guided, this means that the treatment beam follows the changing position of the object. This is also referred to as "tracking".

In one embodiment of the invention, the image data set contains a plurality of three-dimensional images of at least the part of the body containing the object, at different points in time, for example at different stages in the patient's breathing cycle. Such an image data set is also referred to as a 4D image data set. The three-dimensional image for which the virtual projection (DRR) exhibits the greatest match with the images of the imaging devices is for example selected from the images of the imaging devices. The position of the object can then be determined from this three-dimensional image. To this end, the three-dimensional image is preferably segmented such that the voxels of the image data set are assigned to different structures, including the object.

When using a 4D image data set, a cumulative measure of the visibility over a plurality of or all of the three-dimensional images in the 4D image data set is preferably used. To this end, the visibilities of the object in the individual three-dimensional images are determined for an alignment being examined, and the cumulative visibility is ascertained from the individual visibilities. The cumulative visibility is for example the sum of the visibilities, the weighted or unweighted average of the visibilities, or the lowest visibility in the three-dimensional images. Alternatively, the three-dimensional images in the 4D image data set which are determined are those in which the visibility of the object is below a threshold value. The alignments which can be determined as preferred alignments are for example only those for which the visibility is above the threshold value in a minimum number of three-dimensional images in the 4D image data set. Optionally, the treatment beam is guided according to the object but switched off when the visibility of the object is below a threshold value, since the position of the object cannot then be reliably determined. This corresponds to a combination of tracking and gating.

In one embodiment of the invention, a number of preferred alignments are determined and displayed to a user in order for one or more alignments to be selected. Thus, preferred alignments are automatically pre-selected, from which the user can select one or more for the subsequent irradiation. The visibility of the object is for example indicated to the user quantitatively or qualitatively, for example in percent, for each preferred alignment from the number of alignments. Alternatively or additionally, the virtual image—i.e. the projection image (DRR)—which corresponds to the image of an imaging device for the corresponding alignment of the treatment beam generator is displayed. Also alternatively or additionally, the treatment beam generator is moved into each of the alignments, an image is generated by means of each of the imaging devices, and said image is displayed. The user can thus assess the actual visibility of the object in the images of the imaging devices for each alignment from the number of alignments. Advantageously, the object is highlighted in color in virtual images.

In another embodiment of the invention, an optimum alignment is automatically selected from the alignments determined as preferred alignments. The alignment which results in the maximum visibility of the object in the images of the imaging devices is for example selected. If a plurality of imaging devices are provided, then the greatest visibility from all of the images, a weighted or unweighted average of the visibilities in all of the images or the visibility in the image having the lowest visibility of the object serves as the criterion. The selected alignment is preferably displayed to the user, for example together with the quantitative indication of the visibility, the virtual image for a viewing direction corresponding to the selected alignment or the images of the imaging devices for the selected alignment.

The visibility of the object is advantageously defined as the part of the object which is visible in an (actual or virtual) image, in relation to the overall size of the object. The visible part and the overall size can be two-dimensional, i.e. can for example correspond to the area of the object in a two-dimensional image, or can be three-dimensional, i.e. can relate to the volume of the object, wherein the data set comprising the three-dimensional image is preferably segmented in order to obtain the contour of the object. This contour is for example projected onto the DRR. The contours of the (segmented) object in the three-dimensional image and of the object which is visible in the DRR projection image are compared with each other, and a percentage match which quantifies the visibility is calculated from this.

The method in accordance with the invention is in particular a data processing method. The data processing method is preferably performed using technical means, in particular a computer. The computer in particular comprises a processor and in particular a memory in order to process the data, in particular electronically. The calculating or determining steps described are in particular performed by a computer within the framework of the technical data processing method.

The invention also relates to a computer program which, when it is executed in a computational unit, causes the computational unit to perform the method described above.

Within the framework of the invention, computer program elements can be embodied by hardware and/or software (this also includes firmware, resident software, micro-code, etc.). Within the framework of the invention, computer program elements can take the form of a computer program product which can be embodied by a computer-usable or computer-readable storage medium comprising computer-usable or computer-readable program instructions, "code" or a "computer program" embodied in said medium for use on or in connection with the instruction-executing system. Such a system can be a computer; a computer can be a data processing device comprising means for executing the computer program elements and/or the program in accordance with the invention. Within the framework of this invention, a computer-usable or computer-readable medium can be any medium which can include, store, communicate, propagate or transport the program for use on or in connection with the instruction-executing system, apparatus or device. The computer-usable or computer-readable medium can for example be, but is not limited to, an electronic, magnetic, optical, electromagnetic, infrared or semiconductor system, apparatus or device or a medium of propagation such as for example the Internet. The computer-usable or computer-readable medium could even for example be paper or another suitable medium onto which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiments.

The invention also relates to a device for determining preferred alignments of a treatment beam generator, which is suitable for irradiating an object, relative to a body. The device comprises a computational unit which is designed to take into account the visibility of the object in at least one image when determining the preferred alignments. The image is obtained by means of at least one imaging device, the position of which relative to the treatment beam generator is known and invariable. The device and/or components of the device such as the computational unit are correspondingly designed to perform the method described above.

The invention also relates to a treatment device, comprising: a treatment beam generator; at least one imaging device, the position of which relative to the treatment beam generator is known and invariable; and a device for determining preferred alignments. The treatment beam generator and the imaging device(s) are preferably arranged on a common support. A drive for aligning the support relative to the body is preferably also provided. The treatment beam generator can thus be moved into the alignment selected by the user or automatically.

The device preferably comprises an interface via which it is provided with an image data set which represents at least one three-dimensional image of at least a part of the body containing the object. The image data set can for example be provided by an internal or external memory, a network or directly from an image data set generating device such as a computed tomography scanner or magnetic resonance tomography scanner.

The imaging device is preferably an x-ray device. Such an x-ray device usually generates x-ray radiation in the kiloelectron volt (keV) energy range. The x-ray beam is for example conical. Behind the body, the x-ray beam hits a detector which is for example designed two-dimensionally and which captures an x-ray projection image.

The device also preferably comprises an indicating device for indicating proposed or selected preferred alignments. Various ways of indicating the preferred alignments have already been described within the framework of the method.

In one embodiment of the invention, two imaging devices—for example, two x-ray devices—are provided. This enables the location of the object to be more reliably detected, in particular when the object moves along the central axis of the x-ray radiation of one of the x-ray devices. In addition, there is a greater likelihood that at least one of the imaging devices is aligned such that a sufficient visibility of the object in the image which it generates is obtained.

Alternatively or additionally, another sensor is provided which is designed and arranged such that the treatment beam hits the sensor after irradiating the body, and an (additional) image of the body is thus generated. The combination of the treatment beam generator and the additional sensor thus serves as an imaging device.

It is possible within the framework of the invention to omit features which are not necessary for performing the invention or to combine the features described above in any way.

BRIEF DESCRIPTION OF THE DRAWINGS

The present invention shall be explained in more detail on the basis of an example embodiment.

DETAILED DESCRIPTION

Figure 1:
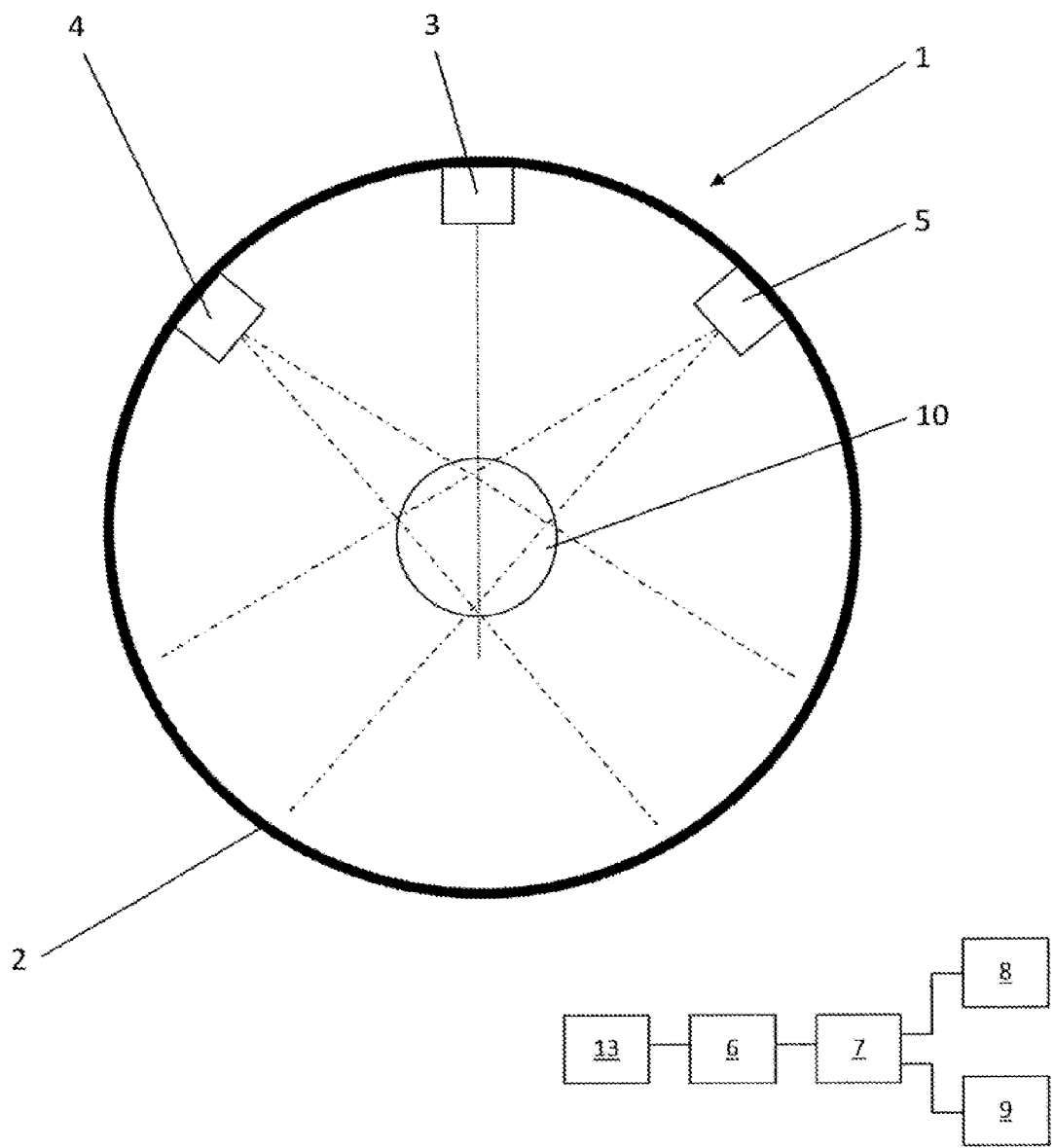
FIG. 1 schematically shows a treatment device in accordance with the invention.

FIG. 1 schematically shows a treatment device 1 comprising a circular support 2 on which a treatment beam generator 3 and two x-ray devices 4 and 5 are arranged. For the sake of clarity, FIG. 1 shows only the x-ray sources and not the corresponding x-ray detectors. The x-ray sources of the x-ray devices 4 and 5 are arranged on both sides, offset by 45 degrees relative to the treatment beam generator 3. The distance between the x-ray devices and the treatment beam generator can also be selected otherwise, for example between 0 and 90 degrees, in particular from 45 degrees to 90 degrees. The support 2 can, in addition to the shape of a circle shown by way of example, also for example exhibit the shape of a circular arc.

A computational unit 6 is connected, via lines (not shown), to the treatment beam generator 3, the x-ray devices 4 and 5 and a drive unit (not shown) for the support 2. The drive unit is capable of rotating the support 2 and the components arranged on it about a longitudinal axis which in the present example is perpendicular to the plane of the paper and passes through the centre point of the circular support 2. Optionally, the support 2 can be tilted about a tilting axis which intersects the longitudinal axis at a right angle and lies horizontally in the plane of the paper in the present representation.

The x-ray sources of the x-ray devices 4 and 5 generate conical x-ray beams which are indicated by dot-dash lines in FIG. 1. The central axis of the conical x-ray beam is also referred to as the viewing direction of the x-ray device. In the present example embodiment, the treatment beam generator generates a pencil beam—shown as a dotted line—in the MeV range, but can also generate a conical beam, depending on the embodiment.

The treatment beam of the treatment beam generator 3 serves to irradiate an object, for example a tumor, in or on a body 10. The x-ray devices 4 and 5 generate images in the form of x-ray images of the body 10. The position of the x-ray devices 4 and 5 relative to the treatment beam generator 3 is invariable and known.

The computational unit 6 is also connected to an interface 7. Via the interface 7, the computational unit 6 is provided with an image data set which represents a three-dimensional image of at least a part of the body 10 containing the object. The image data set is for example stored in a memory 8 and is transferred to the computational unit 6 via the interface 7. Alternatively or additionally, the computational unit 6 is connected via the interface 7 to a magnetic resonance tomography scanner or computed tomography scanner 9 which records and provides the image data set.

One or more alignments of the treatment beam generator 3 relative to the body 10 are to be determined prior to irradiating the body 10 with the treatment beam. This is also referred to as planning, wherein particular care is to be taken that the treatment beam hits as few organs at risk as possible, in order to avoid damaging said organs. The location of the object is ascertained during irradiation, in order to be able to determine whether the treatment beam is hitting the object. To this end, x-ray images of the body 10 are obtained by means of the x-ray devices 4 and 5. Ascertaining the location of an object on the basis of the x-ray images is known from the prior art, for example from European patent applications EP 08 169 422.6 and EP 07 150 014.4 belonging to the Applicant. These documents are hereby incorporated into the present document by reference. The procedure when determining the location of the object from the images is therefore not discussed further.

The location of the object is in particular ascertained repeatedly, in order for example to be able to track a shift in the object due to a breathing movement of the patient.

In order to be able to determine the location of the object from the x-ray images, it is advantageous for as large a part of the object as possible to be visible in the x-ray images. This is for example not the case when the object is hidden by dense structures such as for example bones. The invention is therefore geared not only to the criterion of the organs at risk, but also to the visibility of the object in the x-ray images of the x-ray devices 4 and 5, when determining the alignment of the treatment beam generator 3 relative to the body 10. Since the position of the x-ray devices 4 and 5 relative to the treatment beam generator 3 is invariable, the viewing directions of the x-ray devices 4 and 5 are known for a given alignment of the treatment beam generator 3. It is therefore possible in the planning phase to calculate a virtual image, which corresponds to the x-ray image of an x-ray device 4 or 5, from the three-dimensional image data set of the body 10, for an alignment of the treatment beam generator 3. Calculating a virtual image, which is also referred to as a DRR, from a three-dimensional image data set is known in the prior art and is therefore not described in detail here.

Figure 2A:
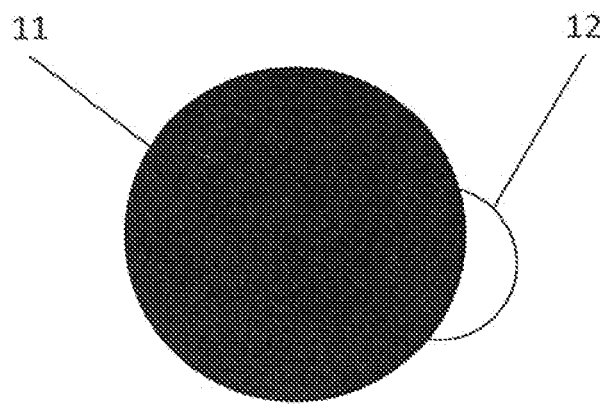
FIG. 2a shows a first virtual image.
Figure 2B:
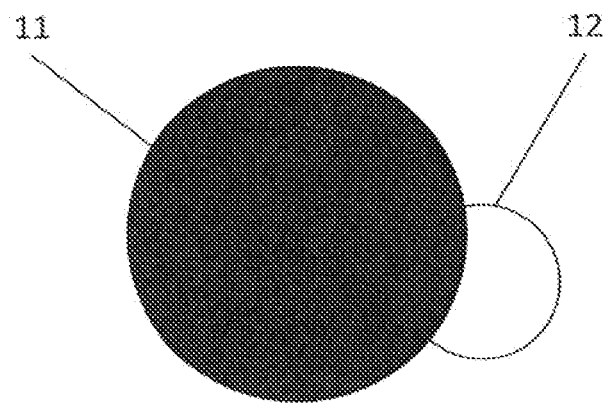
FIG. 2b shows a second virtual image.

FIGS. 2a and 2b schematically show a portion from an x-ray image, from two different viewing directions. The reference sign 11 indicates a blocking structure such as a bone; the reference sign 12 indicates the object to be irradiated. Given the viewing direction on which FIG. 2a is based, about 30% of the object 12 is visible, while in the representation in FIG. 2b, about 60% is visible. In the present example embodiment, the visibility relates to the proportion of the visible area of the object 12 in the x-ray image. If the alignments of the treatment beam generator 3 which result in the viewing directions in FIGS. 2a and 2b are equally suitable with respect to the organs at risk, then the alignment which results in the viewing direction of FIG. 2b is advantageously selected, since a larger part of the object 12 is visible using this alignment, and the location of the object 12 can thus be determined more reliably than in the case of the viewing direction on which FIG. 2a is based.

The statements made with respect to the viewing directions on the basis of FIGS. 2a and 2b relate to an individual one of the x-ray devices 4 or 5. If both x-ray devices are taken into account, there are a number of ways of assessing the visibility. In a first variant, the alignment of the treatment beam generator 3 which results in a viewing direction of an x-ray device which as a whole achieves the greatest visibility of the object 12 in all the images is selected. In a second variant, the visibilities of the object 12 in the images for each alignment of the treatment beam generator 3 are averaged, and the alignment which results in the greatest average visibility is selected. In a third variant, the lowest visibility of the object 12 in all the images is ascertained for each alignment of the treatment beam generator 3, and the alignment having the greatest minimum visibility is selected.

The computational unit 6 is also connected to an indicating device 13. The computational unit 6 is for example designed to display the virtual image or virtual images, which follow from one or more automatically selected alignments of the treatment beam generator 3, on the indicating device 13. This allows a user of the treatment device 1 to check the selected alignments.

Alternatively or additionally, the computational unit is designed to generate a number of possible alignments of the treatment beam generator 3 and output them on the indicating device 13, for example in the form of the virtual image(s) corresponding to the respective alignment.

Optionally, the virtual images are verified by the imaging devices—in the present example embodiment, by the x-ray devices 4 and 5. To this end, the treatment beam generator 3 is aligned in accordance with the alignment, and x-ray images are generated by means of the x-ray devices 4 and 5. These actual x-ray images are then compared with the virtual images calculated for this alignment from the three-dimensional image data set. To this end, the actual x-ray images and optionally the corresponding virtual images are for example indicated on the indicating device 13.

In order to restrict the computational requirement when determining the preferred alignments of the treatment beam generator, the number of alignments examined is preferably restricted, for example to 50, 100, 200, 500 or 1000 alignments.

The example embodiment described above is merely an example and in this respect is not to be understood as limiting. More or less than two x-ray devices can in particular be provided. Alternatively or additionally, a sensor can be provided which detects the treatment beam after it has irradiated the body and thus, together with the treatment beam generator, constitutes an imaging device.

Computer program elements of the invention may be embodied in hardware and/or software (including firmware, resident software, micro-code, etc.). The computer program elements of the invention may take the form of a computer program product which may be embodied by a computer-usable or computer-readable storage medium comprising computer-usable or computer-readable program instructions, "code" or a "computer program" embodied in said medium for use by or in connection with the instruction executing system. Within the context of this application, a computer-usable or computer-readable medium may be any medium which can contain, store, communicate, propagate or transport the program for use by or in connection with the instruction executing system, apparatus or device. The computer-usable or computer-readable medium may for example be, but is not limited to, an electronic, magnetic, optical, electro-magnetic, infrared or semiconductor system, apparatus, device or medium of propagation, such as for example the Internet. The computer-usable or computer-readable medium could even for example be paper or another suitable medium on which the program is printed, since the program could be electronically captured, for example by optically scanning the paper or other suitable medium, and then compiled, interpreted or otherwise processed in a suitable manner. The computer program product and any software and/or hardware described here form the various means for performing the functions of the invention in the example embodiment(s).

Although the invention has been shown and described with respect to one or more particular preferred embodiments, it is clear that equivalent amendments or modifications will occur to the person skilled in the art when reading and interpreting the text and enclosed drawing(s) of this specification. In particular with regard to the various functions performed by the elements (components, assemblies, devices, compositions, etc.) described above, the terms used to describe such elements (including any reference to a "means") are intended, unless expressly indicated otherwise, to correspond to any element which performs the specified function of the element described, i.e. which is functionally equivalent to it, even if it is not structurally equivalent to the disclosed structure which performs the function in the example embodiment(s) illustrated here. Moreover, while a particular feature of the invention may have been described above with respect to only one or some of the embodiments illustrated, such a feature may also be combined with one or more other features of the other embodiments, in any way such as may be desirable or advantageous for any given application of the invention.

What is claimed is:

1. A method for determining preferred alignments of a treatment beam generator relative to a body, the treatment beam generator suitable for irradiating an object, comprising:
    providing an image data set representing a three-dimensional image of at least a part of the body containing the object which is situated in or on the body; and
    determining the preferred alignments based on a degree of visibility of the object in at least one image to be obtained by at least one imaging device which has a known and invariable position relative to the treatment beam generator by determining the visibility of the object from a virtual image calculated from the image data set, the virtual image corresponding to an image captured by an imaging device for a particular alignment of the treatment beam generator.

2. The method according to claim 1, wherein determining the preferred alignments includes taking into account organs at risk in a beam path of the treatment beam generator.

3. The method according to claim 2, wherein determining the preferred alignments includes selecting alignments at which a treatment beam of the treatment beam generator hits as few organs at risk as possible and at which the greatest possible visibility of the object in the images of the imaging devices is simultaneously obtained.

4. The method according to claim 1, further comprising determining a position of the object from the image data set or the at least one image obtained by the at least one imaging device.

5. The method according to claim 4, further comprising automatically switching and/or guiding the treatment beam of the treatment beam generator in accordance with the position of the object.

6. The method according to claim 1, wherein determining the preferred alignment includes determining a number of preferred alignments and displaying the number of preferred alignments for selection by a user.

7. The method according to claim 1, further comprising automatically selecting an optimum alignment from the alignments determined as preferred alignments.

8. The method according to claim 1, wherein the degree of visibility of the object is defined as the part of the object which is visible in an image, in relation to the overall size of the object.

9. A non-transitory computer readable medium comprising computer executable instructions adapted to perform the method according to claim 1.

10. The method according to claim 1, wherein the at least one imaging device is spaced apart from the treatment beam generator.

11. A device for determining preferred alignments of a treatment beam generator relative to a body, the treatment beam generator suitable for irradiating an object which is situated in or on the body, comprising:
    a computational unit configured to
    acquire at least one image data set representing a three-dimensional image of at least a part of the body containing the object via at least one imaging device; and
    determine the preferred alignments based on a degree of visibility of the object in at least one image to be obtained by the at least one imaging device which has a known and invariable position relative to the treatment beam generator by determining the visibility of the object from a virtual image calculated from the at least one image data set, the virtual image corresponding to an image captured by an imaging device for a particular alignment of the treatment beam generator.

12. A treatment device, comprising:
    a treatment beam generator;
    at least one imaging device, the position of which relative to the treatment beam generator is known and invariable; and
    the device according to claim 11.

13. The treatment device according to claim 12, comprising:
    a support, wherein the treatment beam generator and the at least one imaging device are arranged on the support; and
    a drive for aligning the support relative to the body.

14. The device according to claim 11, wherein the imaging device comprises an x-ray device.

15. The device according to claim 11, comprising an indicating device for indicating proposed or selected preferred alignments.

* * * * *